US012635986B2

(12) United States Patent
Shimizu

(10) Patent No.: US 12,635,986 B2
(45) Date of Patent: May 26, 2026

(54) ULTRASOUND IMAGE PROCESSING APPARATUS

(71) Applicant: FUJIFILM Corporation, Tokyo (JP)

(72) Inventor: Motochika Shimizu, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 18/884,315

(22) Filed: Sep. 13, 2024

(65) Prior Publication Data

US 2025/0099078 A1     Mar. 27, 2025

(30) Foreign Application Priority Data

Sep. 25, 2023    (JP) ................................. 2023-160129

(51) Int. Cl.
A61B 8/00          (2006.01)
A61B 8/06          (2006.01)
(52) U.S. Cl.
CPC ................ A61B 8/488 (2013.01); A61B 8/06 (2013.01)
(58) Field of Classification Search
CPC .................................. A61B 8/488; A61B 8/06
See application file for complete search history.

(56) References Cited

U.S. PATENT DOCUMENTS 5,485,844 A    1/1996  Uchibori
5,722,412 A    3/1998  Pflugrath et al.

| 5,779,641 A | 7/1998 | Hatfield et al. | |
| 2001/0009977 A1 | 7/2001 | Sato et al. | |
| 2009/0062654 A1* | 3/2009 | Zhang | G01S 7/5205 |
| | | | 600/455 |
| 2013/0184583 A1* | 7/2013 | Yao | A61B 8/463 |
| | | | 600/443 |
| 2017/0027546 A1* | 2/2017 | Freiburger | A61B 8/5207 |
| 2018/0203104 A1 | 7/2018 | Fujii | |
| 2019/0129020 A1* | 5/2019 | Huang | A61B 8/5207 |
| 2019/0380684 A1* | 12/2019 | Insana | A61B 8/5207 |
| 2020/0022671 A1* | 1/2020 | Noguchi | G01S 15/8984 |
| 2020/0163650 A1* | 5/2020 | Kruger | A61B 5/318 |
| 2020/0184614 A1* | 6/2020 | Zhang | G06T 5/50 |

(Continued)

FOREIGN PATENT DOCUMENTS

| JP | H06-327672 A | 11/1994 |
| JP | H07-051270 A | 2/1995 |

(Continued)

*Primary Examiner* — Sean A Frith
(74) *Attorney, Agent, or Firm* — Paul Teng

(57) ABSTRACT

An ultrasound diagnostic apparatus includes an information processing unit executes processing of acquiring spatial frequency distribution data in a depth direction for Doppler image data, and processing of performing filter processing, which is based on filter characteristics determined in accordance with the spatial frequency distribution data and characteristics of the transmitted ultrasound, on the Doppler image data. The information processing unit searches for a spatial frequency corresponding to a maximal value of a distribution indicated by the spatial frequency distribution data in a search range determined in accordance with a pulse width, and obtains characteristics for suppressing a level of the spatial frequency distribution in a spatial frequency band including the spatial frequency that is searched for.

18 Claims, 15 Drawing Sheets

(56)        References Cited

U.S. PATENT DOCUMENTS

2021/0085287 A1 *   3/2021   Hennersperger ..... A61B 8/5207
2021/0196228 A1      7/2021   Raju et al.

FOREIGN PATENT DOCUMENTS

JP        H10-057375  A      3/1998
JP        H11-028211  A      2/1999
JP        2001-269344 A     10/2001
JP        2004-073620 A      3/2004
JP        2012-254373 A     12/2012
JP        2016-087302 A      5/2016
JP        2020-069304 A      5/2020
JP        2020-537569 A     12/2020
JP        2021-074207 A      5/2021

* cited by examiner

FIG. 11

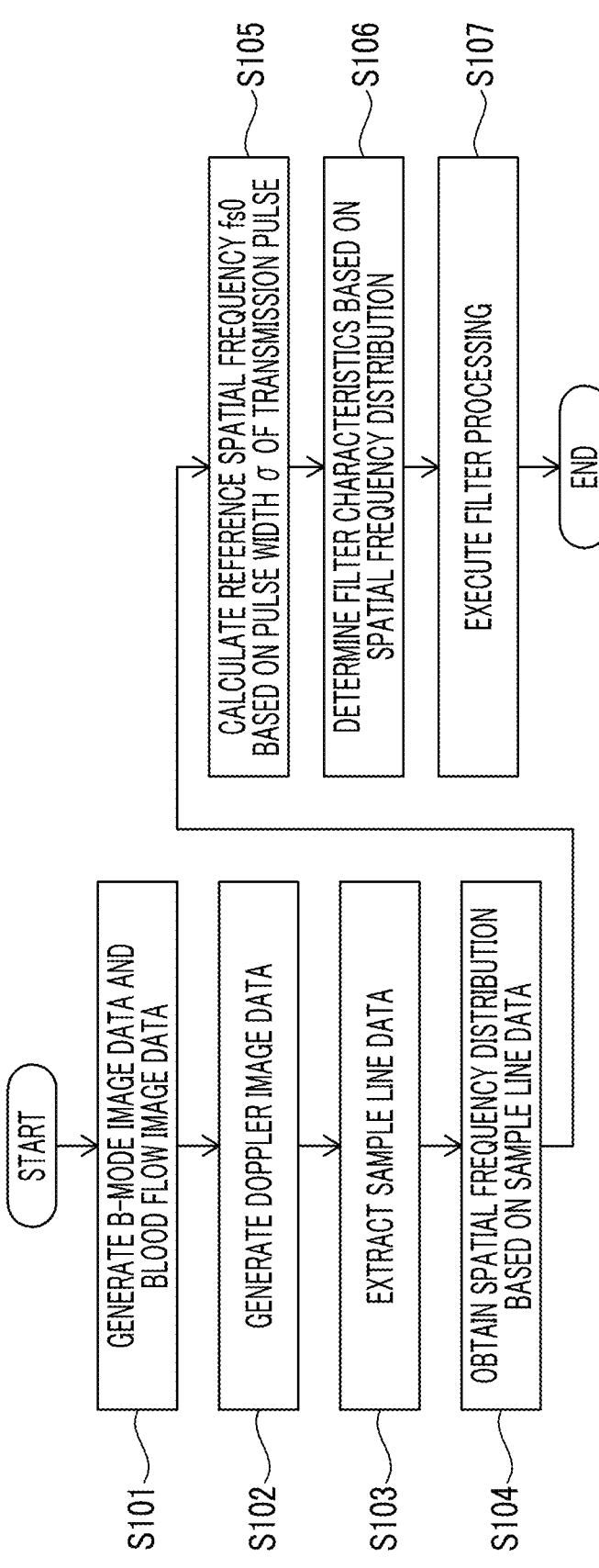

START

S101 GENERATE B-MODE IMAGE DATA AND BLOOD FLOW IMAGE DATA

S102 GENERATE DOPPLER IMAGE DATA

S103 EXTRACT SAMPLE LINE DATA

S104 OBTAIN SPATIAL FREQUENCY DISTRIBUTION BASED ON SAMPLE LINE DATA

S105 CALCULATE REFERENCE SPATIAL FREQUENCY fs0 BASED ON PULSE WIDTH σ OF TRANSMISSION PULSE

S106 DETERMINE FILTER CHARACTERISTICS BASED ON SPATIAL FREQUENCY DISTRIBUTION

S107 EXECUTE FILTER PROCESSING

END

FIG. 14

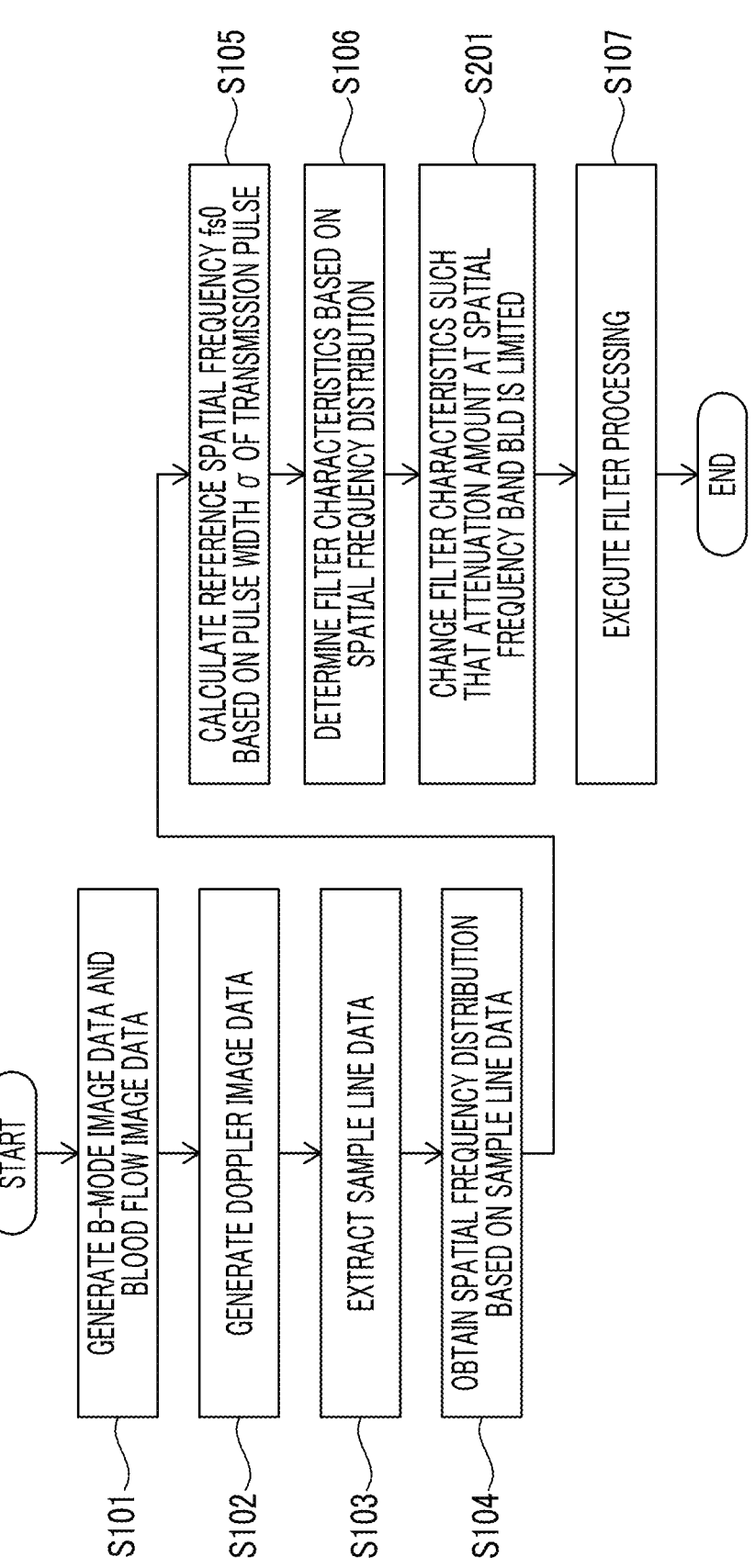

START

S101 — GENERATE B-MODE IMAGE DATA AND BLOOD FLOW IMAGE DATA

S102 — GENERATE DOPPLER IMAGE DATA

S103 — EXTRACT SAMPLE LINE DATA

S104 — OBTAIN SPATIAL FREQUENCY DISTRIBUTION BASED ON SAMPLE LINE DATA

S105 — CALCULATE REFERENCE SPATIAL FREQUENCY fs0 BASED ON PULSE WIDTH σ OF TRANSMISSION PULSE

S106 — DETERMINE FILTER CHARACTERISTICS BASED ON SPATIAL FREQUENCY DISTRIBUTION

S201 — CHANGE FILTER CHARACTERISTICS SUCH THAT ATTENUATION AMOUNT AT SPATIAL FREQUENCY BAND BLD IS LIMITED

S107 — EXECUTE FILTER PROCESSING

END

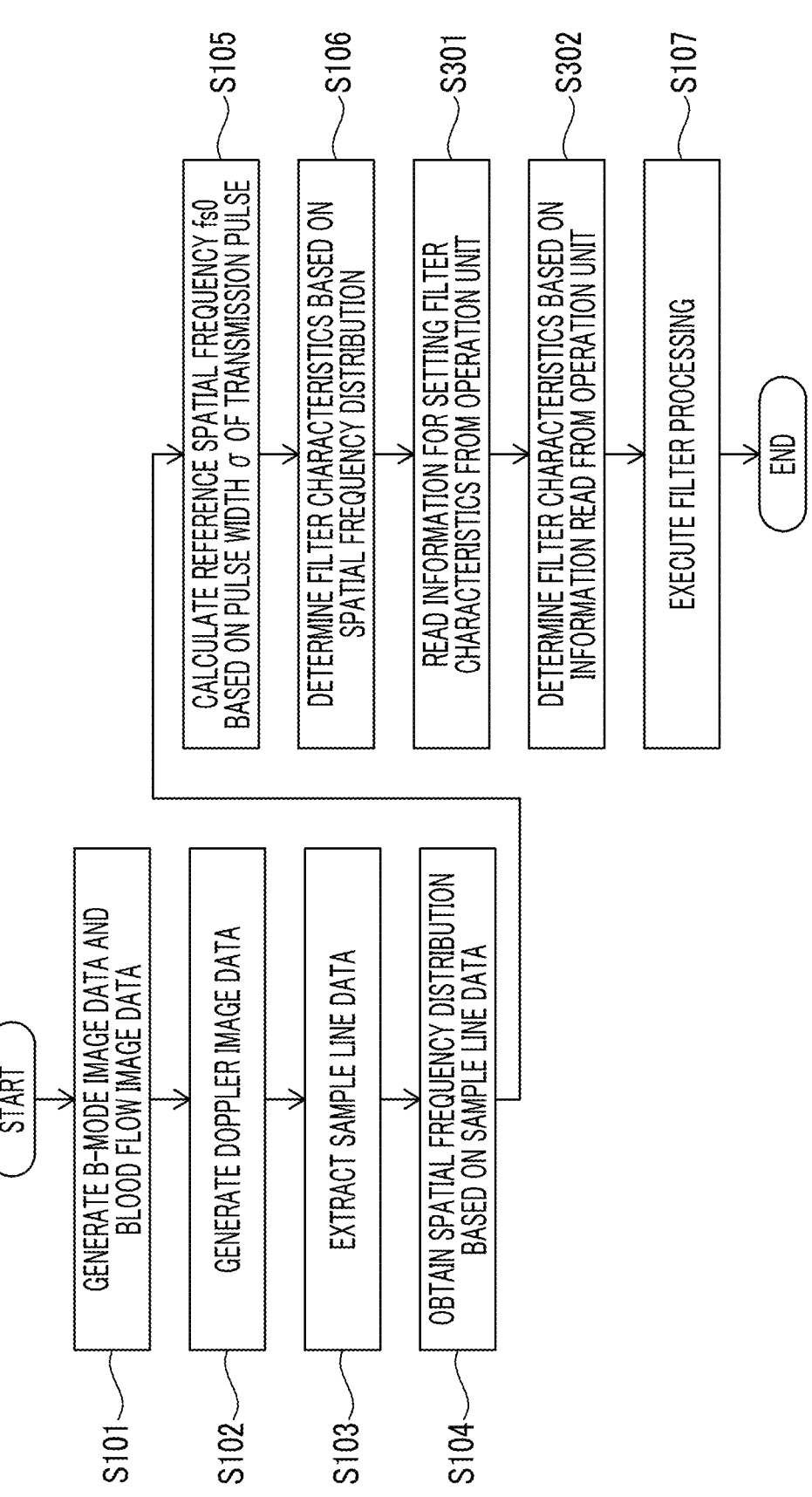

START

S101  GENERATE B-MODE IMAGE DATA AND BLOOD FLOW IMAGE DATA

S102  GENERATE DOPPLER IMAGE DATA

S103  EXTRACT SAMPLE LINE DATA

S104  OBTAIN SPATIAL FREQUENCY DISTRIBUTION BASED ON SAMPLE LINE DATA

S105  CALCULATE REFERENCE SPATIAL FREQUENCY fs0 BASED ON PULSE WIDTH σ OF TRANSMISSION PULSE

S106  DETERMINE FILTER CHARACTERISTICS BASED ON SPATIAL FREQUENCY DISTRIBUTION

S301  READ INFORMATION FOR SETTING FILTER CHARACTERISTICS FROM OPERATION UNIT

S302  DETERMINE FILTER CHARACTERISTICS BASED ON INFORMATION READ FROM OPERATION UNIT

S107  EXECUTE FILTER PROCESSING

END

ULTRASOUND IMAGE PROCESSING APPARATUS

CROSS REFERENCE TO RELATED APPLICATION

The present application claims priority from Japanese Patent Application No. 2023-160129, filed Sep. 25, 2023, the content of which is hereby incorporated by reference into this application.

BACKGROUND OF THE INVENTION

1. Field of the Invention

The present disclosure relates to an ultrasound image processing apparatus, and particularly to processing on Doppler image data.

2. Description of the Related Art

An ultrasound diagnostic apparatus that measures a blood flow velocity of a subject via Doppler measurement is widely used. In such an ultrasound diagnostic apparatus, there is an ultrasound diagnostic apparatus that generates image data indicating a Doppler image in which an image indicating a blood flow velocity in a color is superimposed on a B-mode image.

As shown in JP2016-87302A, in the Doppler measurement, the ultrasound transmission is performed a plurality of times at the same position, and the processing is executed on the reflected waves received a plurality of times. In the ultrasound diagnostic apparatus, the ultrasound that is transmitted earlier is reciprocated, and then the next ultrasound is transmitted. Therefore, there is an upper limit on the number of times of transmission and reception per unit time, and there is also an upper limit on a frame rate. Therefore, in order to increase the frame rate, an interval in a case of scanning with a transmission beam is increased as compared with processing of generating only the B-mode image data, and the number of transmission beams per frame is decreased as compared with a case of generating only the B-mode image data. Further, a resolution of the Doppler image is improved by forming a plurality of reception beams for one transmission beam, and generating image data indicating the blood flow velocity based on a plurality of reception signals obtained from the plurality of reception beams, that is, signals obtained by parallel reception phasing.

It should be noted that JP2020-69304A discloses that, as a technology related to the present disclosure, filter processing is performed on a spatial frequency distribution for two axes of a depth direction and an azimuthal angle direction of an ultrasound image.

SUMMARY OF THE INVENTION

In the ultrasound image such as the B-mode image and the Doppler image generated by the parallel reception phasing, due to the pixel value undulating in the depth direction in which the ultrasound is transmitted and received, as well as in a scanning direction of the transmission beam (azimuthal angle direction in sector scanning), spot-like speckles extending in the scanning direction may be generated. As a result, a stripe pattern extending in the scanning direction may appear as an artifact. The stripe pattern tends to be more remarkable as the scanning interval of the transmission beam is larger.

An object of the present disclosure is to suppress an artifact caused by a pixel value undulating in a depth direction of an ultrasound image.

An aspect of the present disclosure relates to an ultrasound image processing apparatus comprising: an information processing unit that executes processing of acquiring spatial frequency distribution data in a depth direction for Doppler image data generated by transmitting and receiving ultrasound, and processing of performing filter processing, which is based on filter characteristics determined in accordance with the spatial frequency distribution data and characteristics of the transmitted ultrasound, on the Doppler image data.

In one embodiment, that the information processing unit searches for a spatial frequency corresponding to a maximal value of a distribution indicated by the spatial frequency distribution data in a search range determined in accordance with a pulse width of the transmitted ultrasound, and obtains, as the filter characteristics, characteristics for suppressing a level of the distribution indicated by the spatial frequency distribution data in a spatial frequency band including the spatial frequency that is searched for.

In one embodiment, that the information processing unit changes the filter characteristics in a case in which the maximal value of the distribution indicated by the spatial frequency distribution data does not satisfy a predetermined condition for the spatial frequency distribution data acquired from the Doppler image data on which the filter processing has been performed.

In one embodiment, the information processing unit generates the Doppler image data in sequence with elapse of time, and performs the filter processing, which is the same as the filter processing on the Doppler image data of one frame generated earlier, on the Doppler image data of one frame generated later.

In one embodiment, the information processing unit performs the filter processing in which the filter characteristics are changed on the Doppler image data of one frame generated much later in a case in which a condition related to an artifact is not satisfied for the Doppler image data of the one frame generated later.

In one embodiment, the Doppler image data is obtained by transmitting and receiving the ultrasound while performing scanning with a transmission beam of the ultrasound at a predetermined scanning interval, and the information processing unit performs the filter processing on the Doppler image data in a case in which the scanning interval exceeds a predetermined scanning interval threshold value.

In one embodiment, that the scanning interval threshold value is determined based on the characteristics of the transmitted ultrasound.

In one embodiment, the filter characteristics are characteristics for making an attenuation amount in a spatial frequency band corresponding to a blood flow width be equal to or less than an attenuation amount limit value.

In one embodiment, the information processing unit presents at least one of a distribution indicated by the spatial frequency distribution data or the filter characteristics to a user.

In one embodiment, a man-machine interface that changes the filter characteristics in accordance with an operation of the user is configured.

According to the aspect of the present disclosure, it is possible to suppress the artifact caused by the pixel value undulating in the depth direction of the ultrasound image.

BRIEF DESCRIPTION OF THE DRAWINGS

FIG. 11 is a flowchart of processing of determining unnecessary component suppression filter characteristics and performing filter processing on Doppler image data.

FIG. 14 is a flowchart of processing of determining the unnecessary component suppression filter characteristics and performing the filter processing on the Doppler image data.

FIG. 16 is a diagram showing an example of an image showing the spatial frequency distribution and the unnecessary component suppression filter characteristics along with the Doppler image.

FIG. 17 is a flowchart of processing of determining the unnecessary component suppression filter characteristics and performing the filter processing on the Doppler image data.

DESCRIPTION OF THE PREFERRED EMBODIMENTS

Figure 1:
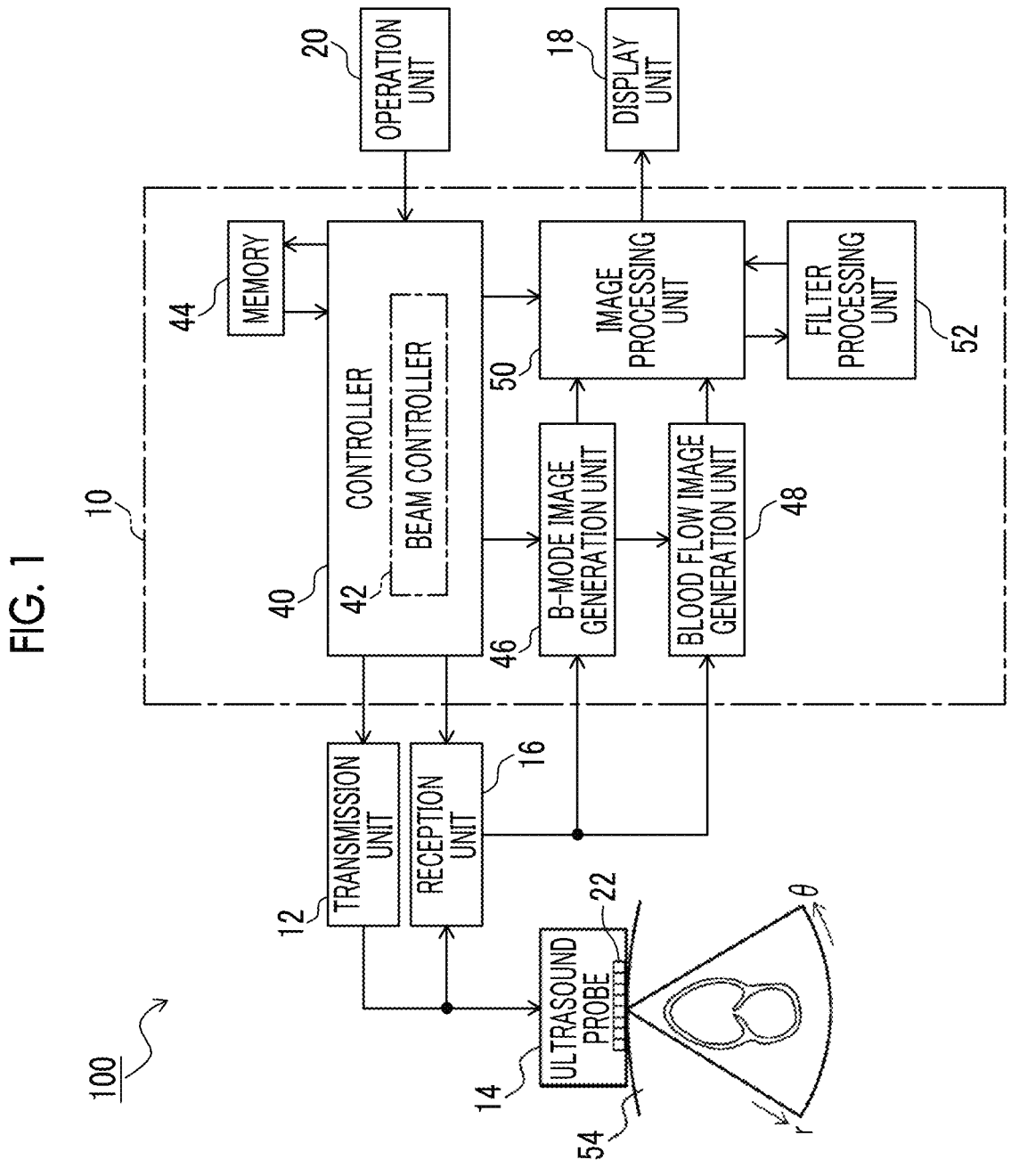
FIG. 1 is a diagram showing a configuration of an ultrasound diagnostic apparatus according to an embodiment of the present disclosure.

An embodiment of the present disclosure will be described with reference to the respective drawings. The same components shown in a plurality of drawings will be denoted by the same reference numerals, and the description thereof will be omitted. It should be noted that, in the present specification, for a term "P image data" for specifying certain image data, an image indicated by the P image data will be referred to as a P image.

FIG. 1 shows a configuration of an ultrasound diagnostic apparatus 100 according to the embodiment of the present disclosure. The ultrasound diagnostic apparatus 100 comprises an information processing unit 10, a transmission unit 12, an ultrasound probe 14, a reception unit 16, a display unit 18, and an operation unit 20. The information processing unit 10 comprises a controller 40, a memory 44, a B-mode image generation unit 46, a blood flow image generation unit 48, an image processing unit 50, and a filter processing unit 52, and constitutes an ultrasound image processing apparatus that executes processing related to an ultrasound image.

The information processing unit 10 may be configured by one or a plurality of processors that execute a program to realize functions of the controller 40, the B-mode image generation unit 46, the blood flow image generation unit 48, the image processing unit 50, and the filter processing unit 52. The program may be stored in the memory 44.

The controller 40 performs overall control on the ultrasound diagnostic apparatus 100. The operation unit 20 includes a keyboard, a mouse, a lever, a button, and the like, and outputs information related to an operation of a user to the controller 40. In a case in which the display unit 18 includes a touch panel on a display screen, the operation unit 20 may include the touch panel. The controller 40 may control the ultrasound diagnostic apparatus 100 in accordance with an operation on the operation unit 20.

An outline of the operation of the ultrasound diagnostic apparatus 100 will be described. The ultrasound diagnostic apparatus 100 transmits ultrasound from the ultrasound probe 14 to a subject 54 and receives the ultrasound reflected by the subject 54 via the ultrasound probe 14. The ultrasound diagnostic apparatus 100 executes each measurement in a B-mode and a Doppler mode. The ultrasound diagnostic apparatus 100 generates B-mode image data based on the ultrasound reflected by the subject 54 in an operation in the B-mode, and displays a B-mode image on the display unit 18. In an operation in the Doppler mode, the ultrasound diagnostic apparatus 100 generates Doppler image data of an inside of the subject 54 based on a Doppler shift frequency of the ultrasound received from the subject 54, and displays a Doppler image on the display unit 18. Only one of the operation in the B-mode or the operation in the Doppler mode may be executed, or the measurement in these two modes may be performed in time division.

A specific configuration of the ultrasound diagnostic apparatus 100 and specific processing executed by the ultrasound diagnostic apparatus 100 will be described. The ultrasound probe 14 is in a state of being in contact with a surface of the subject 54. The ultrasound probe 14 comprises a plurality of oscillating elements 22. The transmission unit 12 outputs a transmission signal to each oscillating element 22 of the ultrasound probe 14 based on control via a beam controller 42 provided in the controller 40. As a result, the ultrasound is transmitted from the ultrasound probe 14. The beam controller 42 forms a transmission beam in the ultrasound probe 14 to scan the subject 54 with the transmission beam by controlling the transmission unit 12. That is, the transmission unit 12 adjusts a delay time or a level of each transmission signal in accordance with the control of the beam controller 42, forms the transmission beam in the ultrasound probe 14, and scans the subject 54 with the transmission beam.

In a case in which the ultrasound reflected in the subject 54 is received by each oscillating element 22 of the ultrasound probe 14, each oscillating element 22 outputs an electric signal corresponding to the received ultrasound to the reception unit 16. The reception unit 16 performs processing, such as amplification, detection, and frequency band limitation, on the reception signal output from each oscillating element 22 in accordance with the control of the beam controller 42. The reception unit 16 further performs phasing addition on the reception signals output from the respective oscillating elements 22 to generate a post-phasing reception signal. As a result, the post-phasing reception signals in which the phases are adjusted and added such that the reception signals based on the ultrasound received from a specific direction reinforce each other are generated, and a reception beam is formed in the specific direction. The reception unit 16 outputs the post-phasing reception signal to the B-mode image generation unit 46 in a case of the operation in the B-mode, and outputs the post-phasing reception signal to the B-mode image generation unit 46 and the blood flow image generation unit 48 in a case of the operation in the Doppler mode.

The operation in the B-mode will be described. The B-mode image generation unit 46 generates the B-mode image data based on the post-phasing reception signal obtained in each reception beam direction, and outputs the B-mode image data to the image processing unit 50. The B-mode image data based on one scanning with the transmission beam and the reception beam is image data for one frame, and corresponds to one B-mode image.

The beam controller 42, the transmission unit 12, the ultrasound probe 14, the reception unit 16, and the B-mode image generation unit 46 generate the B-mode image data one after another in association with the repetitive scanning with the transmission beam and the reception beam, and output each B-mode image data to the image processing unit 50. The image processing unit 50 generates a video signal for displaying the B-mode image based on the B-mode image data, and outputs the video signal to the display unit 18. The display unit 18 displays the B-mode image based on the video signal.

Next, the operation in the Doppler mode will be described. In the Doppler mode, the transmission unit 12 outputs the transmission signal to each of the oscillating elements 22 of the ultrasound probe 14 a plurality of (N) times such that ultrasound pulses are transmitted N times at repetitive time intervals T in one transmission beam direction. The reception unit 16 generates N types of post-phasing reception signals for the N ultrasound pulses reflected in the subject 54 and received by the ultrasound probe 14.

The reception unit 16 forms a plurality of (M) reception beams for one transmission of the ultrasound pulse. That is, the reception unit 16 performs parallel reception phasing on the plurality of reception signals output from the plurality of oscillating elements 22 to form the M reception beams. In a case in which linear scanning with the transmission beam is performed, the reception unit 16 forms the M reception beams having the same direction as the transmission beam direction and arranged parallel to each other. In a case in which sector scanning with the transmission beam is performed, the reception unit 16 forms the M reception beams arranged at equal azimuthal angle intervals. Here, the azimuthal angle refers to an angle that defines a direction as seen from the center of the sector scanning.

Figure 2:
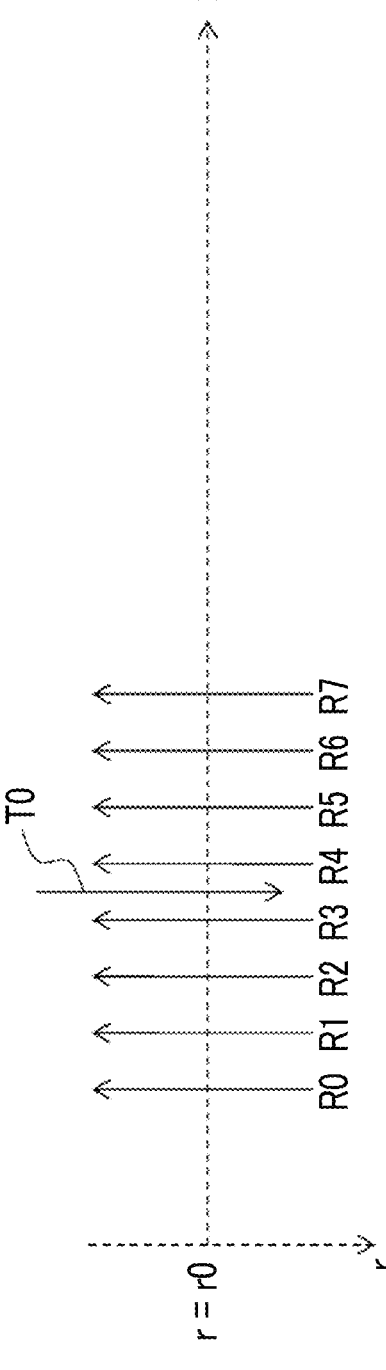
FIG. 2 is a diagram showing an example of a positional relationship between a transmission beam and a plurality of reception beams in a case in which linear scanning is performed.

FIG. 2 shows an example of a positional relationship between a transmission beam T0 and reception beams R0 to R7 in a case in which the linear scanning is performed. As shown in FIG. 2, the transmission beam T0 is formed in a depth direction (r-axis positive direction). In this example, eight (M=8) reception beams R0 to R7 arranged at equal intervals and directed in an r-axis negative direction are formed at a position at which a depth is r=r0 with the transmission beam T0 as a center.

Figure 3:
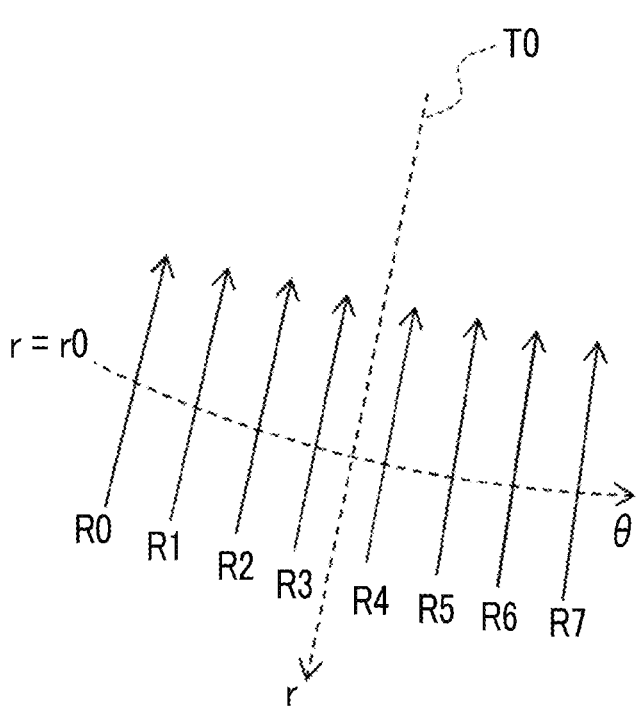
FIG. 3 is a diagram showing an example of a positional relationship between a transmission beam and a plurality of reception beams in a case in which sector scanning is performed.

FIG. 3 shows an example of a positional relationship between the transmission beam T0 and the reception beams R0 to R7 in a case in which the sector scanning is performed. In FIG. 3, the r-axis positive direction is determined in the depth direction, and a θ-axis is determined in an angle direction in which the transmission beam swings. FIG. 3 shows a state in which eight (M=8) reception beams R0 to R7 arranged at equal angle intervals and directed in the r-axis negative direction are formed at a position having a depth of r=r0 with the transmission beam T0 as a center.

The reception unit 16 generates N types of post-phasing reception signals corresponding to the ultrasound pulses transmitted N times for one transmission beam for each of the M reception beams, and outputs the N types of post-phasing reception signals for each of the M reception beams to the blood flow image generation unit 48.

The blood flow image generation unit 48 obtains a blood flow velocity v(r) in the depth direction at each depth r of each of the M reception beams based on the N types of post-phasing reception signals generated for each of the M reception beams, for example, according to the self-correlation processing described in JP2016-87302A.

The blood flow image generation unit 48 generates blood flow image data based on the blood flow velocity v(r) in the depth direction at each depth r of each of the M reception beams. A blood flow image indicated by the blood flow image data is an image indicating a color in accordance with the blood flow velocity v(r) at a position of each depth r on each reception beam. That is, the blood flow image indicates a distribution of the blood flow velocity v(r) in a region in which the M reception beams are disposed by color. In the blood flow image, for example, a blue color is added to a region in which the blood flows in a direction away from the ultrasound probe 14, a red color is added to a region in which the blood flows in a direction close to the ultrasound probe 14, and the brightness is higher in a region in which the blood flow velocity is higher. The blood flow image generation unit 48 outputs the blood flow image data to the image processing unit 50.

The image processing unit 50 generates the Doppler image data based on the B-mode image data and the blood flow image data. The Doppler image data indicates the Doppler image in which the B-mode image and the blood flow image are superimposed on each other. The image processing unit 50 generates the video signal for displaying the Doppler image based on the Doppler image data, and outputs the video signal to the display unit 18. The display unit 18 displays the Doppler image based on the video signal.

In the Doppler image indicated by the Doppler image data generated by the parallel reception phasing, spot-like speckles extending in the scanning direction may be caused by the pixel value undulating in the depth direction as well as the scanning direction of the transmission beam. Here, the scanning direction is a direction perpendicular to the transmission beam in the linear scanning and is an azimuthal angle direction in the sector scanning. Such speckles may cause a stripe pattern extending in the scanning direction to appear as an artifact. This stripe-like artifact tends to be more remarkable as a scanning interval is larger.

Figure 4:
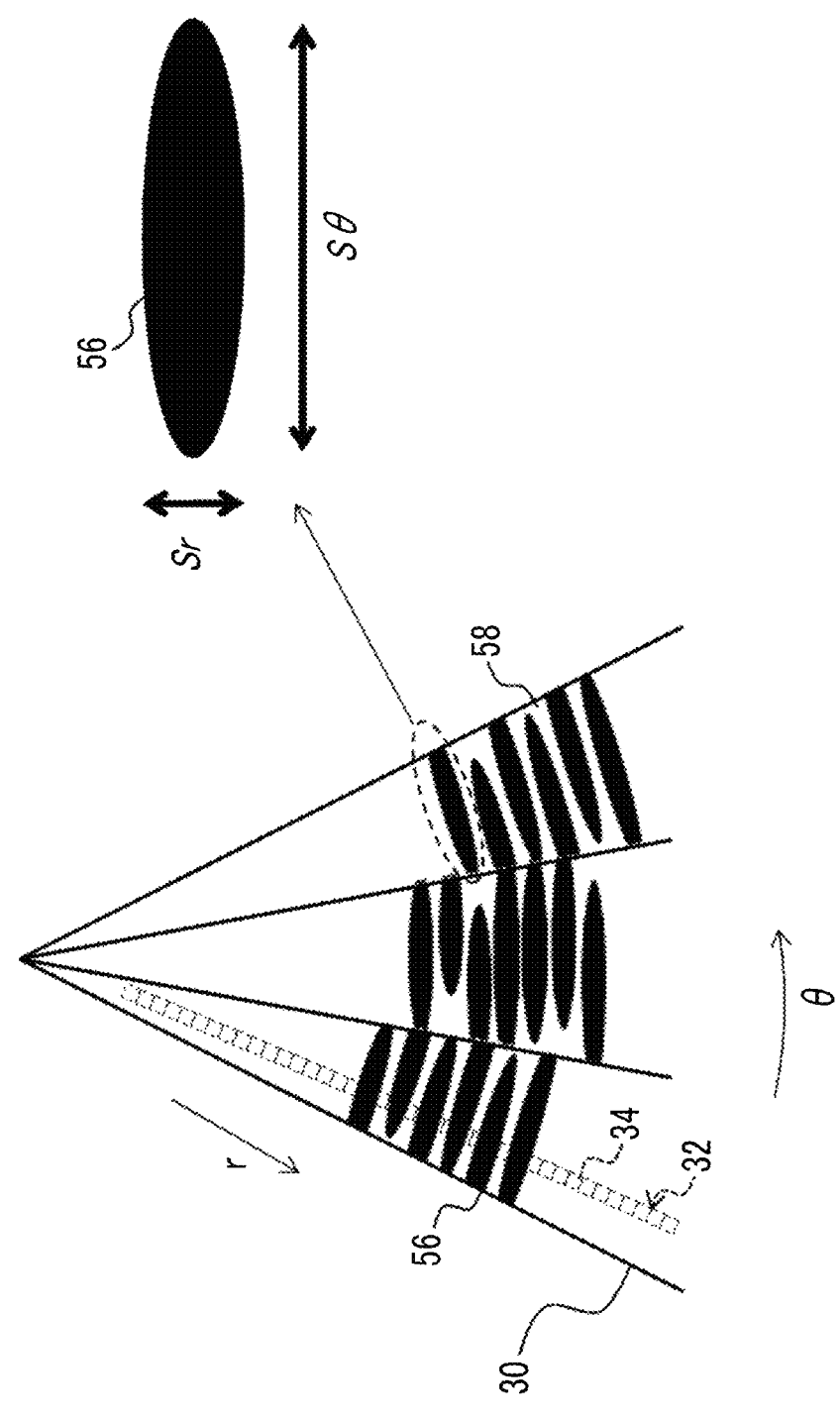
FIG. 4 is a diagram schematically showing a Doppler image and speckles appearing in the Doppler image.

FIG. 4 schematically shows a Doppler image 30 obtained by the sector scanning and speckles 56 appearing in the Doppler image 30. As shown in FIG. 4, the stripe pattern extending in the scanning direction (azimuthal angle direction) appears as the artifact due to gaps 58 among a plurality of speckles 56 extending in the scanning direction. As the scanning interval is larger, the shape of one speckle 56 extending in the scanning direction is more apparent, and the stripe pattern is more remarkable.

Therefore, in the ultrasound diagnostic apparatus 100 according to the present embodiment, the filter processing unit 52 determines filter characteristics for suppressing the stripe-like artifact based on the Doppler image data. The filter processing unit 52 performs the filter processing based on the filter characteristics, on the Doppler image data to generate filter-processed Doppler image data. The image processing unit 50 causes the display unit 18 to display a filter-processed Doppler image. Hereinafter, specific processing is shown.

The image processing unit 50 outputs the Doppler image data to the filter processing unit 52. The filter processing unit 52 extracts depth direction line data representing each pixel value of a plurality of pixels arranged in the depth direction for each of a plurality of azimuthal angle directions from the Doppler image data. In FIG. 4, one set of depth direction line data 32 and pixels 34 arranged in the depth direction are conceptually shown on the Doppler image 30.

The filter processing unit 52 selects one set of a plurality of sets of depth direction line data 32 generated for the plurality of azimuthal angle directions as sample line data. One set of sample line data corresponds to one set of depth direction line data 32 corresponding to one azimuthal angle direction. The filter processing unit 52 performs spatial Fourier transformation on the sample line data to obtain the spatial frequency distribution data.

Figure 5:
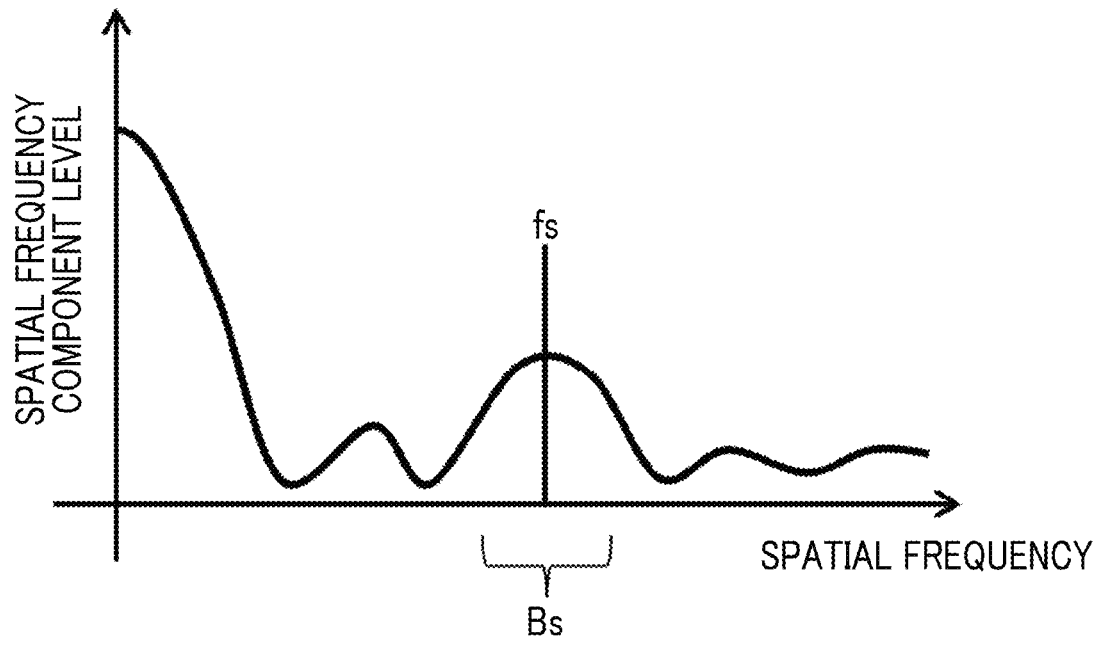
FIG. 5 is a diagram showing an outline of a spatial frequency distribution.

FIG. 5 shows an outline of a distribution (spatial frequency distribution) indicated by the spatial frequency distribution data obtained for the sample line data. A horizontal axis represents a spatial frequency, and a vertical axis represents a level of a spatial frequency component (spatial frequency component level). A speckle spatial frequency fs shown in FIG. 5 corresponds to the maximal value appearing based on the speckles. In addition, a speckle spatial frequency band Bs is a spatial frequency band occupied by the speckles.

The filter processing unit 52 searches for the speckle spatial frequency fs corresponding to the maximal value of the spatial frequency distribution of the sample line data, to define the speckle spatial frequency band Bs including the speckle spatial frequency fs. The filter processing unit 52 further performs the filter processing of suppressing the spatial frequency component of the speckle spatial frequency band Bs on the Doppler image data. Specifically, the filter processing unit 52 performs the filter processing of suppressing the spatial frequency component of the speckle spatial frequency band Bs on the plurality of sets of depth direction line data 32 corresponding to the plurality of azimuthal angle directions extending over the entire region of the Doppler image. As a result, the filter processing unit 52 generates the filter-processed Doppler image data to output the filter-processed Doppler image data to the image processing unit 50. The filter-processed Doppler image data is composed of a plurality of sets of filter-processed depth direction line data obtained by performing the filter processing on the plurality of sets of depth direction line data 32 corresponding to the plurality of azimuthal angle directions extending over the entire region of the Doppler image.

Figure 6:
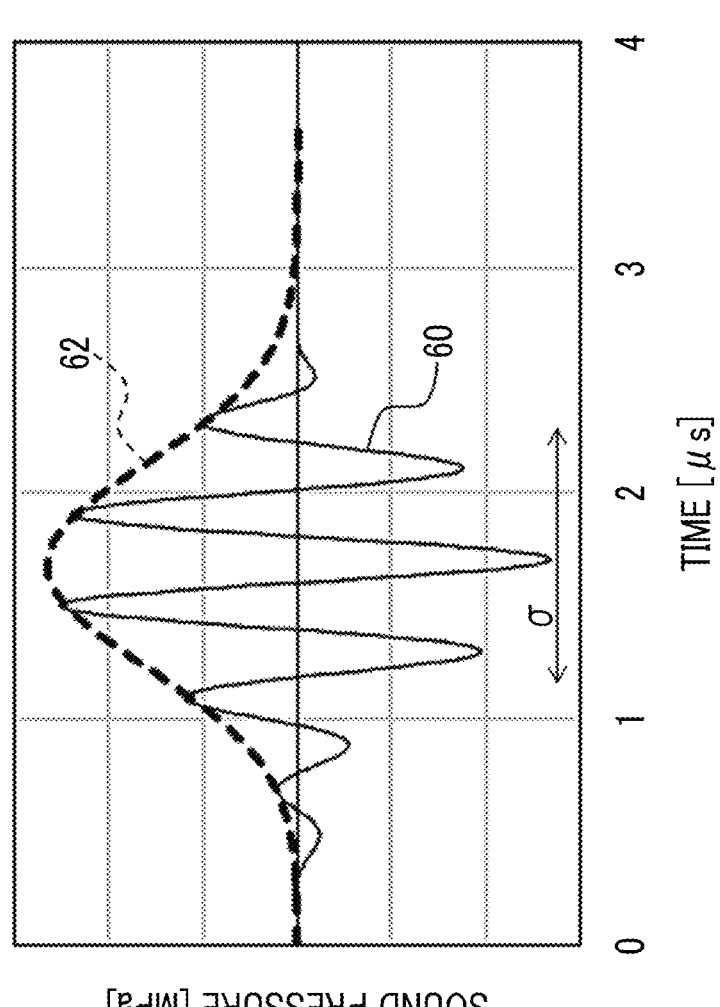
FIG. 6 is a diagram showing an outline of a transmission pulse transmitted from an ultrasound probe.

The processing of searching for the speckle spatial frequency fs, defining the speckle spatial frequency band Bs, and obtaining the filter characteristics will be described. FIG. 6 schematically shows a transmission pulse 60 transmitted from the oscillating element 22 to generate the Doppler image data. A horizontal axis represents a time, and a vertical axis represents a sound pressure. FIG. 6 shows a pulse width σ as one feature value indicating characteristics of transmitted ultrasound. The pulse width σ is defined, for example, as a time length in which the sound pressure is half of the maximum value for an envelope 62 of the transmission pulse 60. An average value Sr [mm] of widths of the speckles 56 in the depth direction shown in FIG. 4 is approximately represented as (Expression 1) using the pulse width σ [sec] of the transmission pulse and a sound velocity c [mm/sec] in the subject 54.

$$Sr = 2.51 \times \sigma \times c \qquad \text{(Expression 1)}$$

It is known that the speckle spatial frequency fs is close to a reference spatial frequency fs0 obtained by multiplying the sound velocity c by a reciprocal of Sr, as shown in (Expression 2).

$$fs0 = c \times 1/Sr = 1/(2.51\sigma) \qquad \text{(Expression 2)}$$

The filter processing unit 52 acquires the spatial frequency component level corresponding to the spatial frequency while increasing the spatial frequency in sequence from the reference spatial frequency fs0 by a step width δ within the search range including the reference spatial frequency fs0 (within the spatial frequency band determined in accordance with the pulse width of the transmitted ultrasound). In addition, the filter processing unit 52 acquires the spatial frequency component level corresponding to the spatial frequency while decreasing the spatial frequency in sequence from the reference spatial frequency fs0 by the step width δ. The filter processing unit 52 determines the spatial frequency at which the spatial frequency component level is maximal, as the speckle spatial frequency fs.

Figure 7:
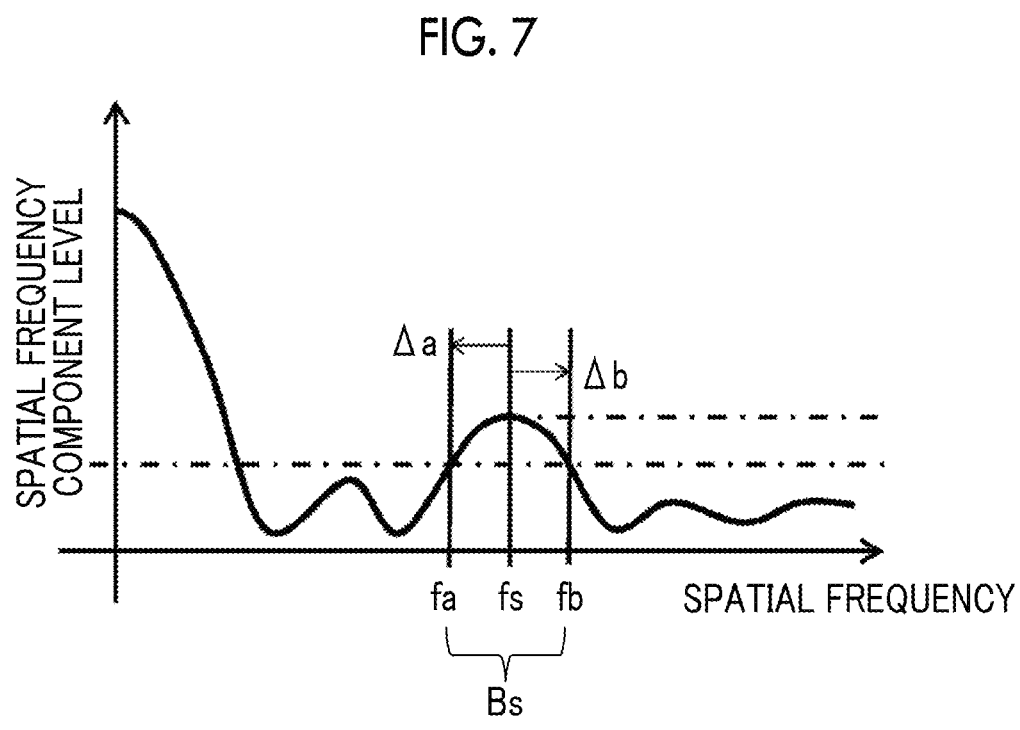
FIG. 7 is a diagram showing a spatial frequency distribution in which a lower limit spatial frequency and an upper limit spatial frequency are shown.

The filter processing unit 52 determines a spatial frequency higher than the speckle spatial frequency fs by a predetermined upper limit spatial frequency width Δb as an upper limit spatial frequency fb of the speckle spatial frequency band Bs, as shown in FIG. 7. In addition, the filter processing unit 52 determines a spatial frequency lower than the speckle spatial frequency fs by a predetermined lower limit frequency width Δa as a lower limit spatial frequency fa of the speckle spatial frequency band Bs.

The filter processing unit 52 forms a band suppression filter in which the speckle spatial frequency band Bs equal to or higher than the lower limit spatial frequency fa and equal to or lower than the upper limit spatial frequency fb is a suppression band width. The band suppression filter has, for example, unnecessary component suppression filter characteristics for suppressing the level by 6 dB or higher in the frequency band equal to or higher than the lower limit spatial frequency fa and equal to or lower than the upper limit spatial frequency fb. The unnecessary component suppression filter characteristics may be characteristics for attenuating the level by 6 dB or higher, preferably 20 dB or higher, at the speckle spatial frequency fs.

Figure 8:
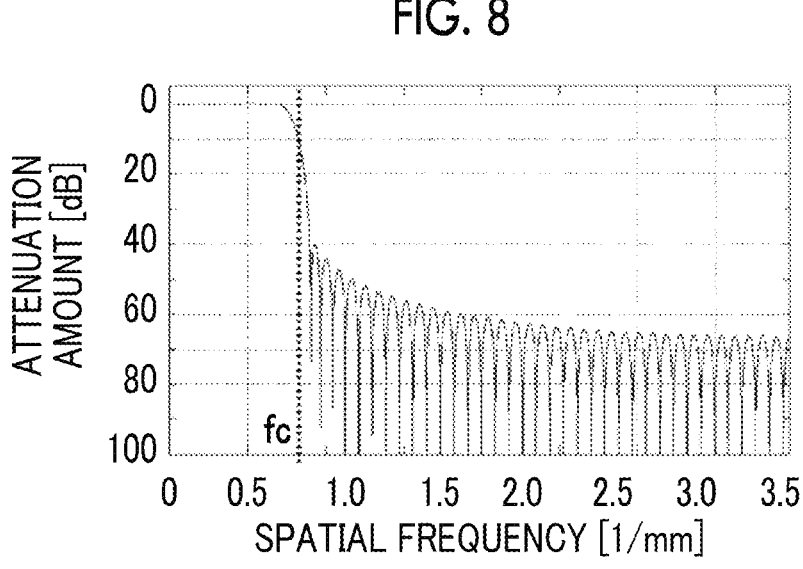
FIG. 8 is a diagram showing low-pass filter characteristics.

FIG. 8 shows low-pass filter characteristics as an example of the unnecessary component suppression filter characteristics. An attenuation amount in a case in which the spatial frequency is 0 is 0 dB, and an attenuation amount of 6 dB or higher is realized in a frequency band equal to or higher than a cutoff spatial frequency fc. The cutoff spatial frequency fc is set to a spatial frequency lower than the lower limit spatial frequency fa. It should be noted that the attenuation amount is a value on a decibel scale that is increased in a positive direction as the attenuation is increased.

Figure 9:
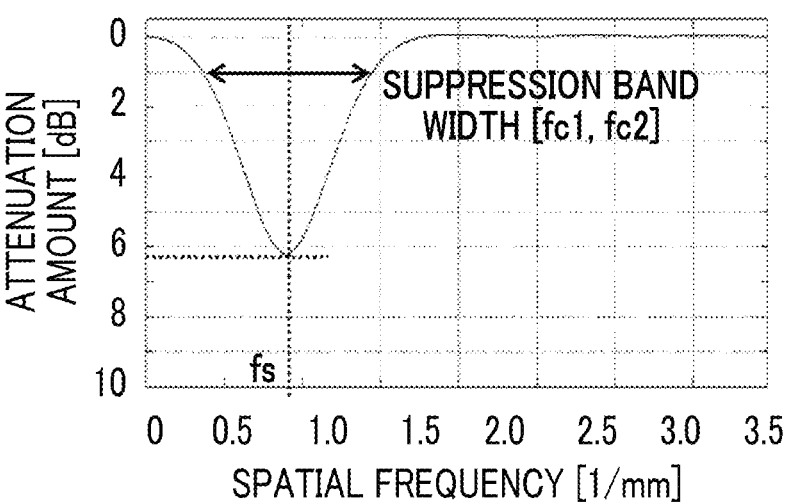
FIG. 9 is a diagram showing band-stop filter characteristics.

FIG. 9 shows band-stop filter characteristics as an example of the unnecessary component suppression filter characteristics. An attenuation amount in a case in which the spatial frequency is 0 and is infinite is set to 0 dB, and an attenuation amount of 6 dB or higher is realized in the spatial frequency band equal to or higher than a low-band cutoff spatial frequency fc1 and equal to or lower than a high-band cutoff spatial frequency fc2. For example, the low-band cutoff spatial frequency fc1 is set to the lower limit spatial frequency fa, and the high-band cutoff spatial frequency fc2 is set to the upper limit spatial frequency fb.

Figure 10:
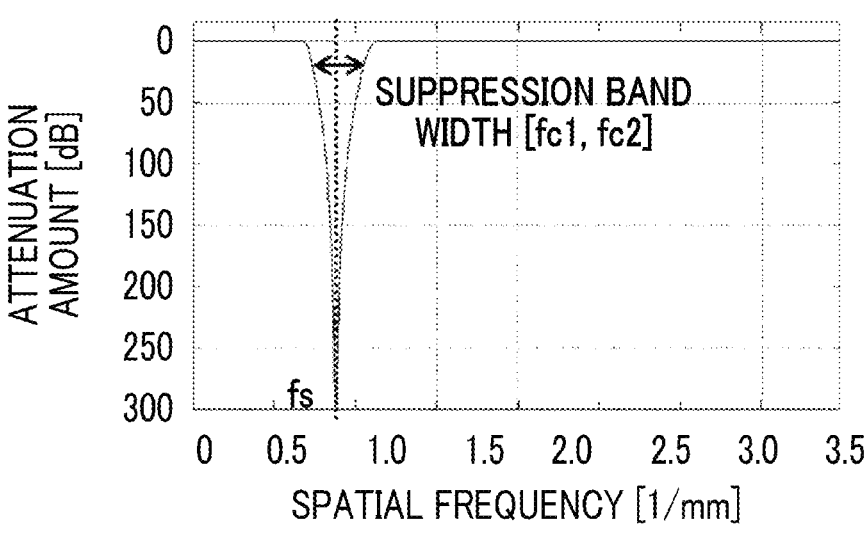
FIG. 10 is a diagram showing notch filter characteristics.

FIG. 10 shows notch filter characteristics as an example of the unnecessary component suppression filter characteristics. The notch filter characteristics are special band-stop filter characteristics. In the notch filter characteristics, a notch in which the attenuation amount is theoretically infinite appears in an attenuation band. For example, the low-band cutoff spatial frequency fc1 is set to the lower limit spatial frequency fa, and the high-band cutoff spatial frequency fc2 is set to the upper limit spatial frequency fb.

The filter processing unit 52 performs the filter processing based on the unnecessary component suppression filter characteristics for each of the plurality of sets of depth direction line data 32 corresponding to the plurality of azimuthal angle directions extending over the entire region of the Doppler image, and generates the plurality of sets of filter-processed depth direction line data corresponding to the plurality of azimuthal angle directions extending over the entire region of the Doppler image. The filter processing unit 52 forms the filter-processed Doppler image data based on the plurality of sets of filter-processed depth direction line data, and outputs the filter-processed Doppler image data to the image processing unit 50. The image processing unit 50 generates the video signal for displaying the filter-processed Doppler image, to output the video signal to the display unit 18. The display unit 18 displays the filter-processed Doppler image based on the video signal.

FIG. 11 shows a flowchart of processing of determining the unnecessary component suppression filter characteristics and performing the filter processing on the Doppler image data. In FIG. 11, the term "unnecessary component suppression filter characteristics" is referred to as "filter characteristics", and the expression is simplified. The B-mode image generation unit 46 and the blood flow image generation unit 48 generate the B-mode image data and the blood flow image data, respectively (S101). The image processing unit 50 generates the Doppler image data based on the B-mode image data and the blood flow image data (S102). The filter processing unit 52 extracts the sample line data from the Doppler image data (S103), and performs the spatial Fourier transformation on the sample line data to obtain the spatial frequency distribution (S104). The filter processing unit 52 calculates the reference spatial frequency fs0 based on the pulse width σ of the transmission pulse in accordance with (Expression 2) (S105). The filter processing unit 52 searches for the speckle spatial frequency fs by using the reference spatial frequency fs0, to determine the unnecessary component suppression filter characteristics (S106). The filter processing unit 52 performs the filter processing on the Doppler image data based on the determined unnecessary component suppression filter characteristics, to generate the filter-processed Doppler image data (S107).

With such processing, as the characteristics of the transmitted ultrasound, the reference spatial frequency fs0 is obtained in accordance with (Expression 2) based on the pulse width σ of the transmission pulse. Then, the speckle spatial frequency fs at which the level is maximal in the spatial frequency distribution is searched for on the high-band side and the low-band side of the reference spatial frequency fs0. Further, the spatial frequency higher than the speckle spatial frequency fs by the predetermined upper limit spatial frequency width Δb is determined as the upper limit spatial frequency fb, the spatial frequency lower than the speckle spatial frequency fs by the predetermined lower limit frequency width Δa is determined as the lower limit spatial frequency fa, and the unnecessary component suppression filter characteristics in the filter processing unit 52 are determined. As a result, the processing of determining the unnecessary component suppression filter characteristics for suppressing the stripe-like artifact is quickly performed.

In the processing, the filter processing unit 52 determines the spatial frequency higher than the speckle spatial frequency fs by the predetermined upper limit spatial frequency width Δb as the upper limit spatial frequency fb, and determines the spatial frequency lower than the speckle spatial frequency fs by the predetermined lower limit frequency width Δa as the lower limit spatial frequency fa. As described above, instead of the processing of determining the spatial frequencies separated from the speckle spatial frequency fs by a certain value as the upper limit spatial frequency fb and the lower limit spatial frequency fa, the following processing may be executed.

That is, the filter processing unit 52 may determine the spatial frequency on the low-band side at which the level of the spatial frequency distribution is decreased by a predetermined ratio with respect to the maximal value of the speckle spatial frequency fs of the spatial frequency distribution, as the lower limit spatial frequency fa. In addition, the filter processing unit 52 may determine the spatial frequency on the high-band side at which the level of the spatial frequency distribution is decreased by a predetermined ratio, as the upper limit spatial frequency fb. As will be described below, the filter processing unit 52 may execute processing of adaptively determining the lower limit spatial frequency fa and the upper limit spatial frequency fb.

The filter processing unit 52 selects a plurality of (K) sets among a plurality of sets of depth direction line data 32 generated for the plurality of azimuthal angle directions as the K sets of sample line data. The filter processing unit 52 performs the spatial Fourier transformation on each of the K sets of sample line data to obtain K types of spatial frequency distributions. The filter processing unit 52 searches for the speckle spatial frequency fs for each of the K types of spatial frequency distributions via the same processing as the processing based on the one set of sample line data. The filter processing unit 52 obtains the minimum speckle spatial frequency fs among the K speckle spatial frequencies fs obtained from the K types of spatial frequency distributions as the lower limit spatial frequency fa, and obtains the maximum speckle spatial frequency fs as the upper limit spatial frequency fb.

Figure 12:
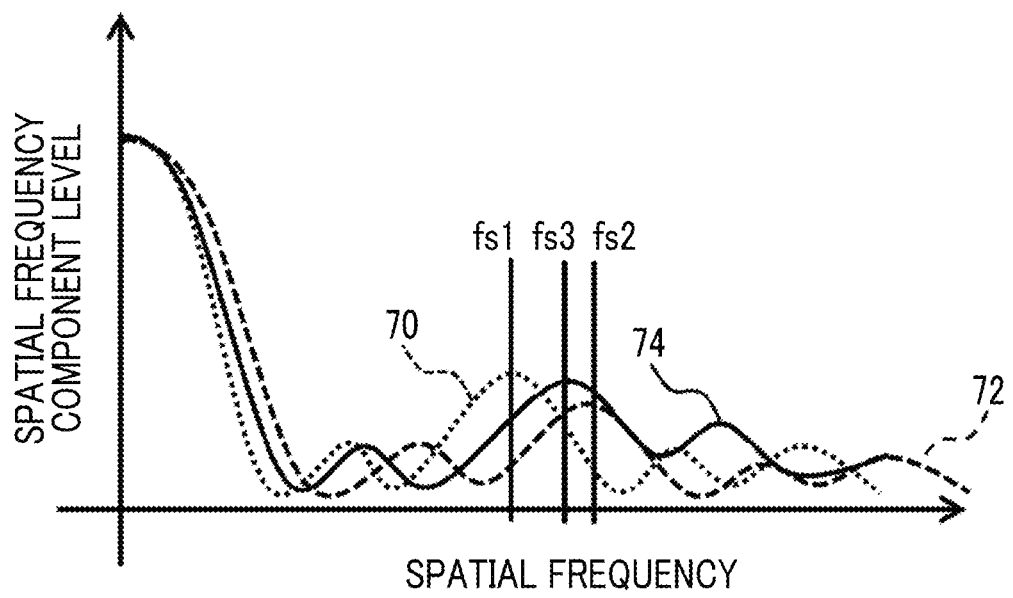
FIG. 12 is a diagram showing a plurality of types of spatial frequency distributions.

FIG. 12 shows a spatial frequency distribution 70 in which a minimum speckle spatial frequency fs1 is obtained, a spatial frequency distribution 72 in which a maximum speckle spatial frequency fs2 is obtained, and a spatial frequency distribution 74 in which a speckle spatial frequency fs3 between the speckle spatial frequency fs1 and the speckle spatial frequency fs2 is obtained. The filter processing unit 52 sets the unnecessary component suppression filter characteristics in the filter processing unit 52 by setting the minimum speckle spatial frequency fs1 as the lower limit spatial frequency fa and the maximum speckle spatial frequency fs2 as the upper limit spatial frequency fb.

The filter processing unit 52 may obtain one spatial frequency distribution by obtaining a statistical value such as an average value, a median value, a maximum value, and a minimum value of K spatial frequency component levels at each spatial frequency, from the K types of spatial frequency distributions obtained from the K sets of sample line data. The filter processing unit 52 may execute the same processing as the processing based on the one set of sample line data for one spatial frequency distribution obtained from the K types of spatial frequency distributions. That is, the filter processing unit 52 may search for the speckle spatial frequency fs for one spatial frequency distribution obtained from the K types of spatial frequency distributions, to obtain the lower limit spatial frequency fa and the upper limit spatial frequency fb.

An image of a blood vessel may appear in the Doppler image. In this case, in the filter-processed Doppler image in which the stripe-like artifact is suppressed, the blood vessel may be difficult to see. Therefore, the filter processing unit 52 may execute processing of limiting the attenuation amount in the spatial frequency band corresponding to the blood flow width.

Figure 13:
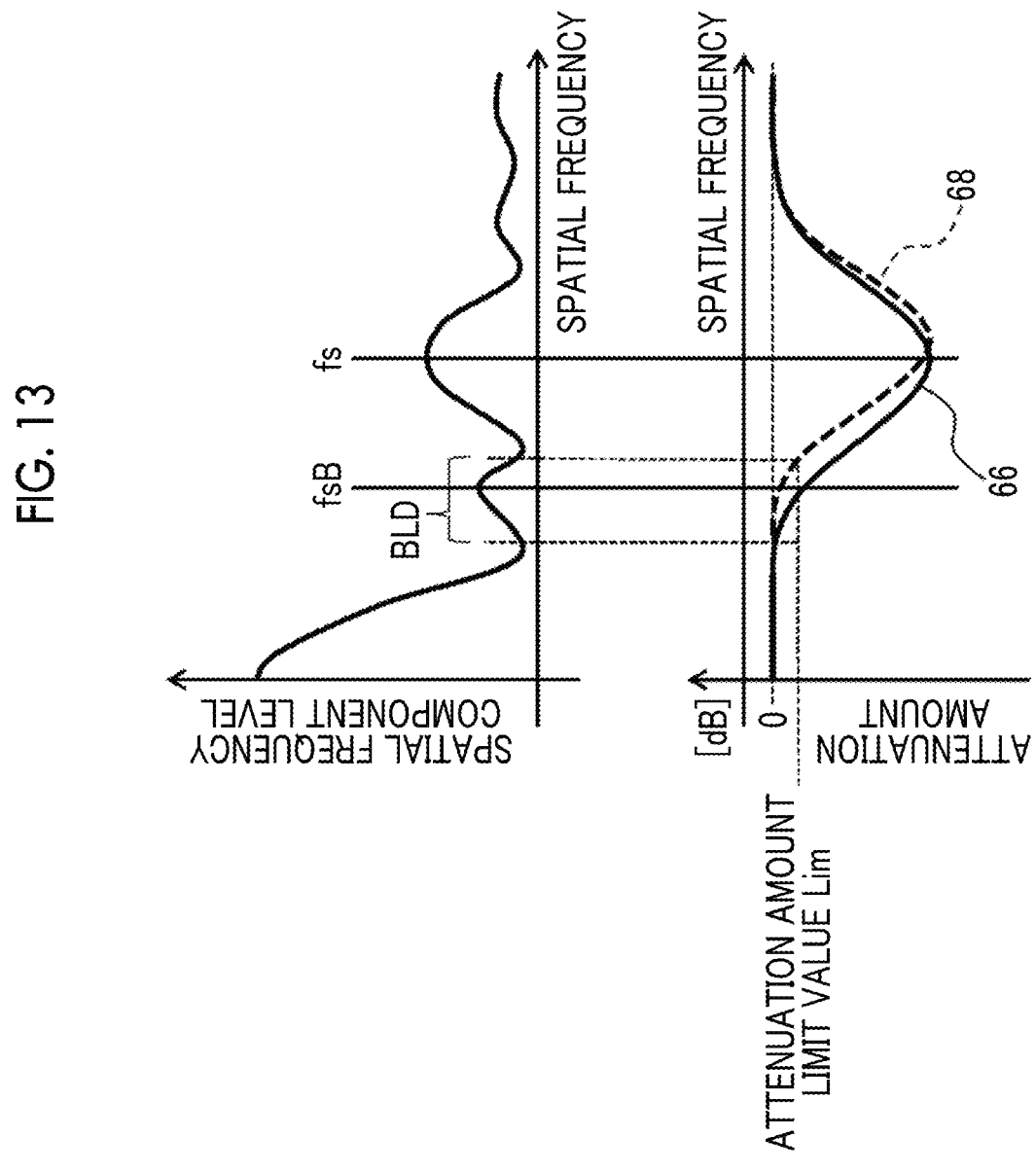
FIG. 13 is a diagram showing an outline of a spatial frequency distribution in a case in which an image of a blood vessel appears in the Doppler image, and the unnecessary component suppression filter characteristics.

An upper part of FIG. 13 shows an outline of the spatial frequency distribution in a case in which the image of the blood vessel appears in the Doppler image. In this spatial frequency distribution, the maximal value appears in the speckle spatial frequency fs, and the maximal value also appears in a blood flow width spatial frequency fsB corresponding to the blood flow width. The controller 40 reads the blood flow width spatial frequency fsB and a spatial frequency band BLD including the blood flow width spatial frequency fsB in accordance with the operation of the operation unit 20 performed by the user. The blood flow width spatial frequency fsB and the spatial frequency band BLD may be stored in the memory 44 in advance and read by the controller 40. The filter processing unit 52 determines the unnecessary component suppression filter characteristics such that the attenuation amount is equal to or less than a predetermined attenuation amount limit value Lim in the spatial frequency band BLD including the blood flow width spatial frequency fsB, based on the control of the controller 40.

A lower part of FIG. 13 shows an example of unnecessary component suppression filter characteristics 66 in which the attenuation amount is not limited in the spatial frequency band BLD and an example of unnecessary component suppression filter characteristics 68 in which the attenuation amount is limited in the spatial frequency band BLD. By performing, via the filter processing unit 52, the filter processing using the unnecessary component suppression filter characteristics 68 on the Doppler image data, the stripe-like artifact that appears in the filter-processed Doppler image is suppressed, and the blood vessel and the blood flow are clearly represented.

FIG. 14 shows a flowchart of processing of determining the unnecessary component suppression filter characteristics and performing the filter processing on the Doppler image data. This flowchart is different from the flowchart shown in FIG. 11 in that step S201 is added between step S106 and step S107. In FIG. 14, the term "unnecessary component suppression filter characteristics" is referred to as "filter characteristics", and the expression is simplified. The filter processing unit 52 searches for the speckle spatial frequency fs using the reference spatial frequency fs0, to determine the unnecessary component suppression filter characteristics (S106), and then changes the unnecessary component suppression filter characteristics such that the attenuation amount in the spatial frequency band BLD is equal to or less than the attenuation amount limit value Lim (S201). The filter processing unit 52 performs the filter processing based on the unnecessary component suppression filter characteristics changed in step S201 on the Doppler image data, to generate the filter-processed Doppler image data (S107).

In the ultrasound diagnostic apparatus 100, the B-mode image generation unit 46 outputs the B-mode image data to the image processing unit 50 in sequence with the elapse of time, and the blood flow image generation unit 48 outputs the blood flow image data to the image processing unit 50 in sequence with the elapse of time. The image processing unit 50 generates the Doppler image data in sequence with the elapse of time to output the Doppler image data to the filter processing unit 52. The filter processing unit 52 performs the filter processing on each of the Doppler image data output from the image processing unit 50 in sequence with the elapse of time, and outputs the filter-processed Doppler image data to the image processing unit 50 in sequence with the elapse of time.

The filter processing unit 52 may perform the filter processing (hereinafter, also referred to as adaptive filter processing) in which filter characteristics are adaptively changed in accordance with the filter-processed Doppler image data generated in the past, on the Doppler image data output in sequence from the image processing unit 50. Further, the filter processing unit 52 may output the filter-processed Doppler image data to the image processing unit 50 in sequence with the elapse of time.

Here, the adaptive filter processing will be described. In the adaptive filter processing, processing of changing the filter characteristics is repeated in a case in which the maximal value of the distribution indicated by the spatial frequency distribution data does not satisfy a predetermined condition, for the spatial frequency distribution data acquired from the filter-processed Doppler image data. Here, the predetermined condition is a condition for suppressing the stripe-like artifact.

Figure 15:
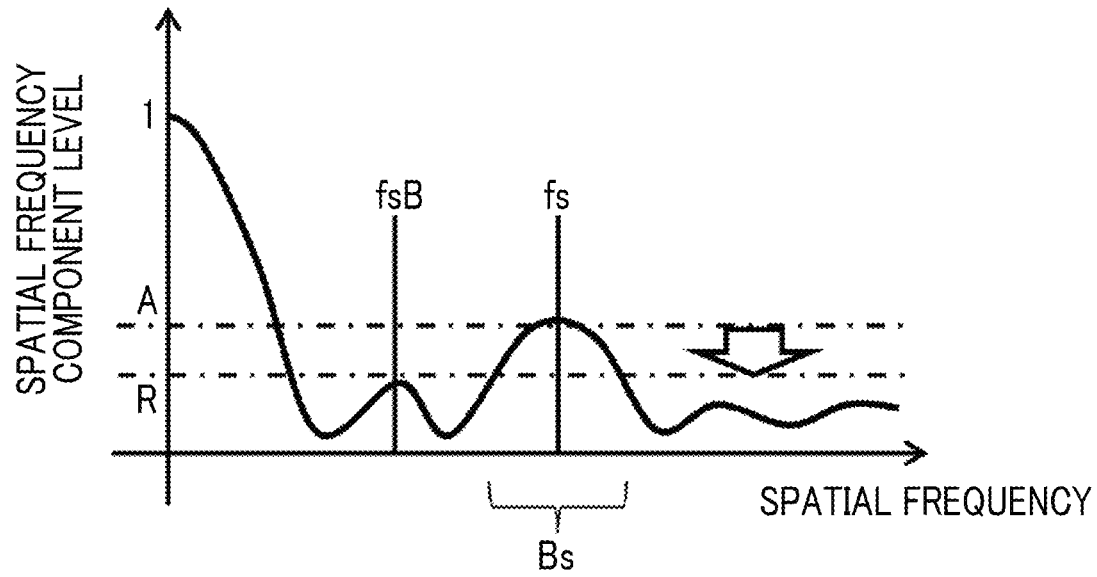
FIG. 15 is a diagram showing an outline of a spatial frequency distribution obtained for one sample line data in Doppler image data of a certain frame.

FIG. 15 shows an outline of the spatial frequency distribution obtained for one sample line data in the filter-processed Doppler image data of a certain frame. The level of the component having the spatial frequency of 0 is standardized to 1, and the maximal value at the speckle spatial frequency fs is A. In a case in which a target value of the level at the speckle spatial frequency fs is R, and R<A is satisfied, the filter processing unit 52 adjusts and changes the unnecessary component suppression filter characteristics such that the attenuation amount at the speckle spatial frequency fs is $20 \log(A/R)$ [dB] or more. Here, log is a logarithmic function with 10 as a base, and the attenuation amount is a value that is larger in the positive direction as the attenuation is larger.

The filter processing unit 52 performs the filter processing based on the unnecessary component suppression filter characteristics changed based on the earlier Doppler image data, on the Doppler image data of one frame output later from the image processing unit 50, and outputs the filter-processed Doppler image data to the image processing unit 50. In a case in which R<A is satisfied again in the spatial frequency distribution obtained for one sample line data in the filter-processed Doppler image data of one frame output to the image processing unit 50, the filter processing unit 52 changes the unnecessary component suppression filter characteristics such that the attenuation amount at the speckle spatial frequency fs is 20 log(A/R) or more.

In this way, the filter processing unit 52 sets the unnecessary component suppression filter characteristics based on the earlier data in the filter-processed Doppler image data generated in sequence with the elapse of time, and performs the filter processing based on the determined filter characteristics, on the Doppler image data of the next frame. The filter processing unit 52 executes such processing in sequence on the Doppler image data generated in sequence with the elapse of time, so that the unnecessary component suppression filter characteristics converge to ideal characteristics.

From another viewpoint, the filter processing unit 52 executes the following processing. That is, the filter processing unit 52 performs the same filter processing as the filter processing on the Doppler image data of one frame generated earlier, on the Doppler image data of one frame generated later. In a case in which the condition related to the artifact is not satisfied for the Doppler image data of one frame generated later, the filter processing unit 52 performs the filter processing in which the filter characteristics are changed, on the Doppler image data of the frame generated much later. The condition related to the artifact is, for example, a condition in which the maximal value A and the target value R at the speckle spatial frequency fs satisfy A≤R for the spatial frequency distribution obtained for one sample line data.

Whether or not the filter processing is performed on the Doppler image data may be determined in accordance with the scanning interval. For example, the filter processing may be performed in a case in which the scanning interval in the azimuthal angle direction exceeds a predetermined scanning interval threshold value. In a case in which the scanning interval exceeds the predetermined scanning interval threshold value, the controller 40 causes the image processing unit 50 and the filter processing unit 52 to execute the filter processing. On the other hand, in a case in which the scanning interval is equal to or less than the scanning interval threshold value, the controller 40 does not cause the image processing unit 50 and the filter processing unit 52 to execute the filter processing on the Doppler image data, and displays the Doppler image based on the Doppler image data on which the filter processing has not been performed, on the display unit 18.

The scanning interval threshold value may be determined based on a theoretical value of the magnitude of the speckles 56 in the scanning direction. An average value Sθ [mm] of the widths of the speckles 56 in the scanning direction is approximately represented as (Expression 3). Here, λ is a wavelength [mm] of the ultrasound, z is a measurement depth [mm], and D is an opening width [mm]. The opening width D is a length in which the plurality of oscillating elements 22 provided in the ultrasound probe 14 are arranged on a surface scanned with the ultrasound beam.

$$S\theta = 0.9\lambda z/D \qquad \text{(Expression 3)}$$

In a case in which the width of the speckle 56 in the scanning direction is expressed by the azimuthal angle, a scanning interval threshold value θt [rad] may be obtained in accordance with (Expression 4).

$$\theta t \approx \arctan(S\theta/z) = \arctan(0.9\lambda/D) \qquad \text{(Expression 4)}$$

In the ultrasound diagnostic apparatus 100, a man-machine interface that changes the unnecessary component suppression filter characteristics in accordance with the operation of the user may be configured. The man-machine interface may be configured by the image processing unit 50, the display unit 18, and the operation unit 20. That is, the unnecessary component suppression filter characteristics may be set based on the operation of the operation unit 20 performed by the user who refers to the display unit 18. For example, the controller 40 may read the attenuation amounts at the speckle spatial frequency fs, the lower limit spatial frequency fa, the upper limit spatial frequency fb, and the speckle spatial frequency band, the attenuation amounts at the blood flow width spatial frequency fsB and the spatial frequency band BLD including the blood flow width spatial frequency fsB, and the like, in accordance with the operation of the operation unit 20. In this case, the image processing unit 50 may display at least one of the spatial frequency distribution obtained for the sample line data or the unnecessary component suppression filter characteristics on the display unit 18, and may present the at least one of the spatial frequency distribution or the unnecessary component suppression filter characteristics to the user. The unnecessary component suppression filter characteristics may be represented by a graph in which a horizontal axis is the spatial frequency and a vertical axis is the attenuation amount, the phase rotation amount, and the like.

Figure 16:
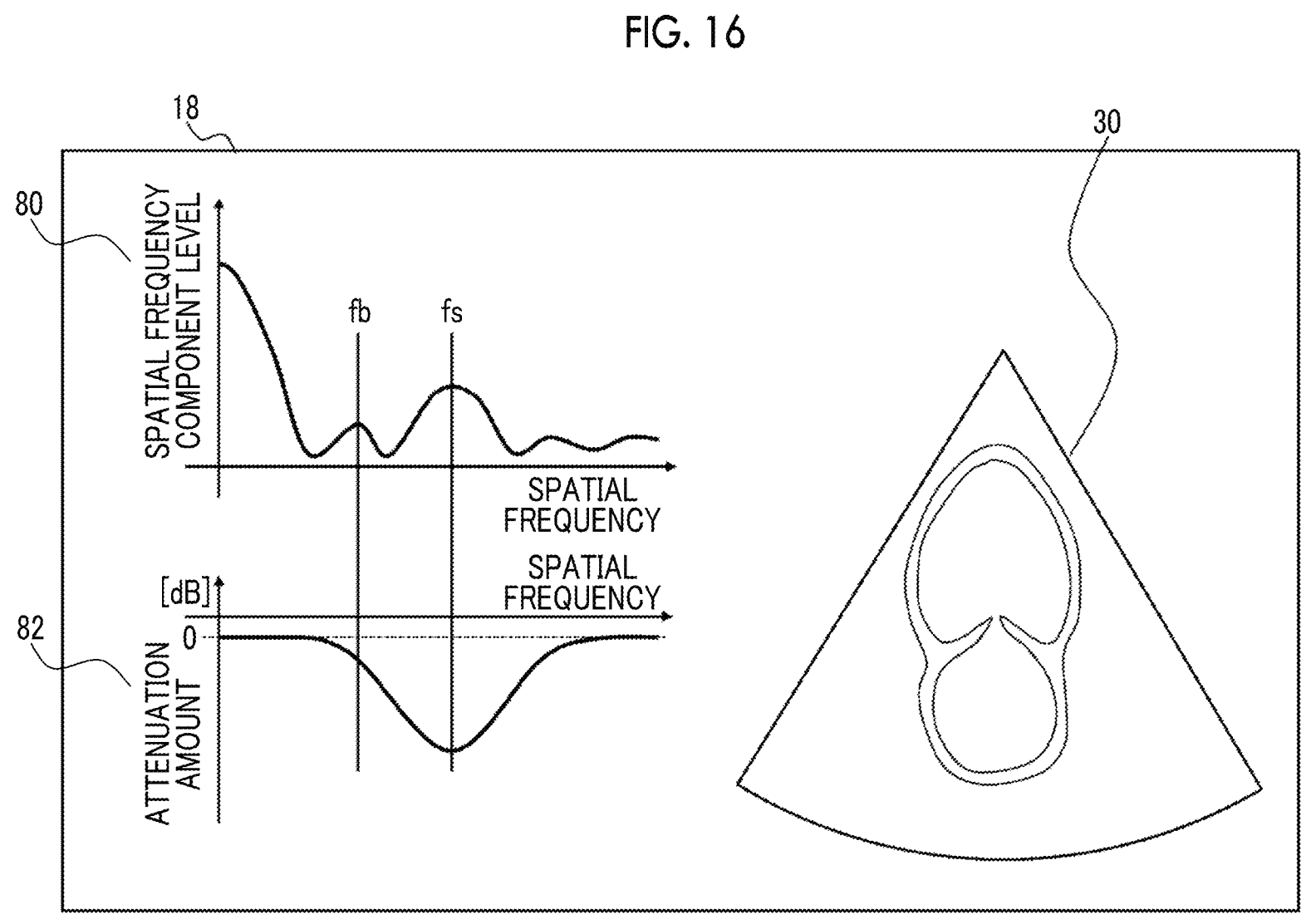

FIG. 16 shows an example of an image showing a spatial frequency distribution 80 and unnecessary component suppression filter characteristics 82 together with the Doppler image 30. It should be noted that the image processing unit 50 may display the actually applied unnecessary component suppression filter characteristics, the type of the filter (low-pass filter, band-stop filter, notch filter, or the like), and the like on the display unit 18 by text information or the like.

A graphical user interface displayed on the display unit 18 in a case in which the unnecessary component suppression filter characteristics are set may include, for example, a button, an icon, or the like in which "none", "weak", "medium", "strong", or the like is displayed. In addition, the image processing unit 50 may display a graphical user interface for setting the unnecessary component suppression filter characteristics on the display unit 18 via the operation unit 20.

FIG. 17 shows a flowchart of processing of determining the unnecessary component suppression filter characteristics and performing the filter processing on the Doppler image data. This flowchart is different from the flowchart shown in FIG. 11 in that steps S301 and S302 are added between steps S106 and S107. In addition, the term "unnecessary component suppression filter characteristics" is referred to as "filter characteristics", and the expression is simplified. The filter processing unit 52 searches for the speckle spatial frequency fs by using the reference spatial frequency fs0, to determine the unnecessary component suppression filter characteristics (S106), and further reads information for setting the unnecessary component suppression filter characteristics from the operation unit 20 (S301). The filter processing unit 52 changes the unnecessary component suppression filter characteristics based on the information read from the operation unit 20 (S302). The filter processing unit 52 performs the filter processing based on the unnecessary component suppression filter characteristics changed in step S302 on the Doppler image data, to generate the filter-processed Doppler image data (S107).

Configuration of Present Disclosure

Configuration 1:

An ultrasound image processing apparatus comprising: an information processing unit that executes processing of acquiring spatial frequency distribution data in a depth direction for Doppler image data generated by transmitting and receiving ultrasound, and processing of performing filter processing, which is based on filter characteristics determined in accordance with the spatial frequency distribution data and characteristics of the transmitted ultrasound, on the Doppler image data.

Configuration 2:

The ultrasound image processing apparatus according to configuration 1, in which the information processing unit searches for a spatial frequency corresponding to a maximal value of a distribution indicated by the spatial frequency distribution data in a search range determined in accordance with a pulse width of the transmitted ultrasound, and obtains, as the filter characteristics, characteristics for suppressing a level of the distribution indicated by the spatial frequency distribution data in a spatial frequency band including the spatial frequency that is searched for.

Configuration 3:

The ultrasound image processing apparatus according to configuration 2, in which the information processing unit changes the filter characteristics in a case in which the maximal value of the distribution indicated by the spatial frequency distribution data does not satisfy a predetermined condition for the spatial frequency distribution data acquired from the Doppler image data on which the filter processing has been performed.

Configuration 4:

The ultrasound image processing apparatus according to any one of configurations 1 to 3, in which the information processing unit generates the Doppler image data in sequence with elapse of time, and performs the filter processing, which is the same as the filter processing on the Doppler image data of one frame generated earlier, on the Doppler image data of one frame generated later.

Configuration 5:

The ultrasound image processing apparatus according to configuration 4, in which the information processing unit performs the filter processing in which the filter characteristics are changed on the Doppler image data of one frame generated much later in a case in which a condition related to an artifact is not satisfied for the Doppler image data of the one frame generated later.

Configuration 6:

The ultrasound image processing apparatus according to any one of configurations 1 to 5, in which the Doppler image data is obtained by transmitting and receiving the ultrasound while performing scanning with a transmission beam of the ultrasound at a predetermined scanning interval, and the information processing unit performs the filter processing on the Doppler image data in a case in which the scanning interval exceeds a predetermined scanning interval threshold value.

Configuration 7:

The ultrasound image processing apparatus according to configuration 6, in which the scanning interval threshold value is determined based on the characteristics of the transmitted ultrasound.

Configuration 8:

The ultrasound image processing apparatus according to any one of configurations 1 to 7, in which the filter characteristics are characteristics for making an attenuation amount in a spatial frequency band corresponding to a blood flow width be equal to or less than an attenuation amount limit value.

Configuration 9:

The ultrasound image processing apparatus according to any one of configurations 1 to 8, in which the information processing unit presents at least one of a distribution indicated by the spatial frequency distribution data or the filter characteristics to a user.

Configuration 10:

The ultrasound image processing apparatus according to configuration 9, in which a man-machine interface that changes the filter characteristics in accordance with an operation of the user is configured.

What is claimed is:

1. An ultrasound image processing apparatus comprising: an information processing unit that executes
   processing of acquiring spatial frequency distribution data in a depth direction for Doppler image data generated by transmitting and receiving ultrasound in Doppler measurement, and
   processing of performing filter processing, which is based on filter characteristics determined in accordance with the spatial frequency distribution data and characteristics of the transmitted ultrasound, on the Doppler image data obtained through the Doppler measurement, wherein
   the filter characteristics, in the filter processing performed on the Doppler image data obtained through the Doppler measurement, include characteristics for suppressing a spatial frequency component level of the Doppler image data, in a spatial frequency band including spatial frequencies indicated by the spatial frequency distribution data.

2. The ultrasound image processing apparatus according to claim 1, wherein the information processing unit searches for a spatial frequency corresponding to a maximal value of a distribution indicated by the spatial frequency distribution data in a search range determined in accordance with a pulse width of the transmitted ultrasound, and obtains, as the filter characteristics, characteristics for suppressing a level of the distribution indicated by the spatial frequency distribution data in a spatial frequency band including the spatial frequency that is searched for.

3. The ultrasound image processing apparatus according to claim 2, wherein the information processing unit changes the filter characteristics in a case in which the maximal value of the distribution indicated by the spatial frequency distribution data does not satisfy a predetermined condition for the spatial frequency distribution data acquired from the Doppler image data on which the filter processing has been performed.

4. The ultrasound image processing apparatus according to claim 1, wherein the information processing unit generates the Doppler image data in sequence with elapse of time, and performs the filter processing, which is the same as the filter processing on the Doppler image data of one frame generated earlier, on the Doppler image data of one frame generated later.

5. The ultrasound image processing apparatus according to claim 4, wherein the information processing unit performs the filter processing in which the filter characteristics are changed on the Doppler image data of one frame generated after the one frame generated later is generated, in a case in which a condition related to an artifact is not satisfied for the Doppler image data of the one frame generated later.

6. The ultrasound image processing apparatus according to claim 1, wherein the Doppler image data is obtained by transmitting and receiving the ultrasound while performing scanning with a transmission beam of the ultrasound at a predetermined scanning interval, and the information processing unit performs the filter processing on the Doppler image data in a case in which the scanning interval exceeds a predetermined scanning interval threshold value.

7. The ultrasound image processing apparatus according to claim 6, wherein the scanning interval threshold value is determined based on the characteristics of the transmitted ultrasound.

8. The ultrasound image processing apparatus according to claim 1, wherein the filter characteristics include characteristics for making an attenuation amount in a spatial frequency band corresponding to a blood flow width be equal to or less than an attenuation amount limit value.

9. The ultrasound image processing apparatus according to claim 1, wherein the information processing unit presents at least one of a distribution indicated by the spatial frequency distribution data or the filter characteristics to a user.

10. The ultrasound image processing apparatus according to claim 9, wherein the information processing unit is configured to change the filter characteristics in accordance with an operation of the user.

11. An ultrasound image processing apparatus comprising a processor and a non-transitory medium embodying a program of instructions executable by the processor to configure the ultrasound image processing apparatus to perform a method comprising:

processing of acquiring spatial frequency distribution data in a depth direction for Doppler image data generated by transmitting and receiving ultrasound in Doppler measurement; and processing of performing filter processing, which is based on filter characteristics determined in accordance with the spatial frequency distribution data and characteristics of the transmitted ultrasound, on the Doppler image data obtained through the Doppler measurement, wherein the filter characteristics, in the filter processing performed on the Doppler image data obtained through the Doppler measurement, include characteristics for suppressing a spatial frequency component level of the Doppler image data, in a spatial frequency band including spatial frequencies indicated by the spatial frequency distribution data.

12. The ultrasound image processing apparatus according to claim 11, wherein the method performed by the ultrasound image processing apparatus further comprises:

searching for a spatial frequency corresponding to a maximal value of a distribution indicated by the spatial frequency distribution data in a search range determined in accordance with a pulse width of the transmitted ultrasound; and obtaining, as the filter characteristics, characteristics for suppressing a level of the distribution indicated by the spatial frequency distribution data in a spatial frequency band including the spatial frequency that is searched for.

13. The ultrasound image processing apparatus according to claim 12, wherein the method performed by the ultrasound image processing apparatus further comprises:

changing the filter characteristics in a case in which the maximal value of the distribution indicated by the spatial frequency distribution data does not satisfy a predetermined condition for the spatial frequency distribution data acquired from the Doppler image data on which the filter processing has been performed.

14. The ultrasound image processing apparatus according to claim 11, wherein the Doppler image data is generated in sequence with elapse of time, and the filter processing, which is the same as the filter processing on the Doppler image data of one frame generated earlier, is performed on the Doppler image data of one frame generated later.

15. The ultrasound image processing apparatus according to claim 14, wherein the filter processing is performed in which the filter characteristics are changed on the Doppler image data of one frame generated after the one frame generated later is generated, in a case in which a condition related to an artifact is not satisfied for the Doppler image data of the one frame generated later.

16. The ultrasound image processing apparatus according to claim 11, wherein the Doppler image data is obtained by transmitting and receiving the ultrasound while performing scanning with a transmission beam of the ultrasound at a predetermined scanning interval, and the filter processing is performed on the Doppler image data in a case in which the scanning interval exceeds a scanning interval threshold value which is determined based on the characteristics of the transmitted ultrasound.

17. The ultrasound image processing apparatus according to claim 11, wherein the filter characteristics include characteristics for making an attenuation amount in a spatial frequency band corresponding to a blood flow width be equal to or less than an attenuation amount limit value.

18. The ultrasound image processing apparatus according to claim 11, wherein the method performed by the ultrasound image processing apparatus further comprises:

presenting at least one of a distribution indicated by the spatial frequency distribution data or the filter characteristics to a user; and changing the filter characteristics in accordance with an operation of the user.

* * * * *